(12) United States Patent
Linford

(10) Patent No.: US 10,094,732 B2
(45) Date of Patent: Oct. 9, 2018

(54) PIPELINE FAULT DETECTION SYSTEM, SENSOR HEAD AND METHOD OF DETECTING PIPELINE FAULTS

(75) Inventor: Paul Linford, Norfolk (GB)

(73) Assignee: SYRINIX LIMITED, Norwich, Norfolk (GB)

( * ) Notice: Subject to any disclaimer, the term of this patent is extended or adjusted under 35 U.S.C. 154(b) by 137 days.

(21) Appl. No.: 14/116,276

(22) PCT Filed: May 11, 2012

(86) PCT No.: PCT/GB2012/051057
§ 371 (c)(1),
(2), (4) Date: Mar. 3, 2014

(87) PCT Pub. No.: WO2012/153147
PCT Pub. Date: Nov. 15, 2012

(65) Prior Publication Data
US 2014/0165731 A1    Jun. 19, 2014

(30) Foreign Application Priority Data
May 11, 2011    (GB) .................................. 1107810.2

(51) Int. Cl.
*G01M 3/00*    (2006.01)
*G01M 3/24*    (2006.01)
(Continued)

(52) U.S. Cl.
CPC .............. *G01M 3/00* (2013.01); *G01M 3/243* (2013.01); *G01N 29/024* (2013.01); *G01N 29/07* (2013.01); *G01N 29/14* (2013.01); *G01N 29/4436* (2013.01); *G01N 29/4472* (2013.01); *G01N 29/46* (2013.01); *F17D 5/00* (2013.01); *G01N 2291/2634* (2013.01)

(58) Field of Classification Search
CPC ..... G01M 3/243; G01N 29/024; G01N 29/14; G01N 29/4472
USPC .......................................................... 73/592
See application file for complete search history.

(56) References Cited

U.S. PATENT DOCUMENTS 3,664,357 A * 5/1972 Kreiss ....................... F17D 1/14
137/2
4,356,444 A    10/1982 Saenz, Jr.
(Continued)

FOREIGN PATENT DOCUMENTS

EP    2006654    12/2008
EP    2314997    4/2011
(Continued)

*Primary Examiner* — Lisa Caputo
*Assistant Examiner* — Tarun Sinha
(74) *Attorney, Agent, or Firm* — Leason Ellis LLP

(57) ABSTRACT

A pipeline fault detection system, method and sensor head suitable for use in the system are disclosed. The system comprises a vibro-acoustic sensor connectable to a fluid path of a pipeline and a remote monitoring system, the sensor being operable to measure one or more predetermined vibro-acoustic properties of the fluid and/or fluid path and communicate data on said measurements to the remote monitoring system, the remote monitoring system being arranged to monitor said data over time and being further arranged to screen the monitored data for characteristics representing a fault type to identify occurrence of a fault type in the pipeline.

20 Claims, 10 Drawing Sheets

(51) Int. Cl.
  *G01N 29/024* (2006.01)
  *G01N 29/07* (2006.01)
  *G01N 29/14* (2006.01)
  *G01N 29/44* (2006.01)
  *G01N 29/46* (2006.01)
  *F17D 5/00* (2006.01)

(56) References Cited

U.S. PATENT DOCUMENTS

| | | | |
|---|---|---|---|
| 4,516,206 A | 5/1985 | McEvilly | |
| 4,609,994 A | 9/1986 | Bassim et al. | |
| 5,333,501 A | 8/1994 | Mori et al. | |
| 5,987,990 A | 11/1999 | Worthington | |
| 6,082,193 A | 7/2000 | Paulson | |
| 6,212,133 B1 | 4/2001 | McCoy et al. | |
| 6,253,624 B1* | 7/2001 | Broden | G01F 1/50 73/861.44 |
| 7,470,060 B1* | 12/2008 | Hoben | G01F 9/001 340/870.16 |
| 2006/0005635 A1* | 1/2006 | Breen | G01F 1/6986 73/861.95 |
| 2006/0225507 A1* | 10/2006 | Paulson | F17D 5/02 73/592 |
| 2008/0047329 A1 | 2/2008 | Breed | |
| 2008/0143344 A1* | 6/2008 | Focia | G01M 5/0025 324/642 |
| 2008/0314122 A1* | 12/2008 | Hunaidi | G01M 3/243 73/40.5 A |
| 2009/0000381 A1 | 1/2009 | Allison | |
| 2010/0011869 A1 | 1/2010 | Klosinski et al. | |
| 2011/0156957 A1 | 6/2011 | Waite et al. | |

FOREIGN PATENT DOCUMENTS

| | | |
|---|---|---|
| JP | 11064151 | 3/1999 |
| JP | 2004117174 | 4/2004 |
| RU | 2190152 | 12/2000 |
| WO | WO2009129959 | 10/2009 |
| WO | WO201007637 | 9/2010 |

* cited by examiner

PIPELINE FAULT DETECTION SYSTEM, SENSOR HEAD AND METHOD OF DETECTING PIPELINE FAULTS

CROSS REFERENCE TO RELATED APPLICATIONS

This application is a U.S. National Phase Application under 35 U.S.C. § 371 of International Patent Application No. PCT/GB2012/051057, filed May 11, 2012, and claims priority to Great Britain Application Nos. GB1107810.2, filed May 11, 2011, which are hereby incorporated by reference in their respective entireties herein. The International Application was published as International Publication No. WO2012/153147 under PCT Article 21(2).

FIELD OF THE INVENTION

The present invention relates to a pipeline fault detection system, method and sensor head that are particularly applicable for use in continuous automatic fault detection for pipelines such as trunk mains water supplies.

BACKGROUND TO THE INVENTION

Pipelines are used for delivery of many different fluid types including gasses, water, liquid chemical compositions, liquid foodstuffs, oil and other petroleum based products.

Leakage, fracturing or bursting (referred to as "faults") of a pipeline can have severe consequences. Such faults will almost always have financial implications to the pipeline operator both in terms of loss of fluid to the environment, cost to repair or replace the pipeline and cost to reach the pipeline to effect the repairs and then make good any damaged caused by the repair. Depending on the fluid and its use, there can also be other direct or indirect implications. Direct implications include environmental damage by the leaking fluid (for a petrochemical or chemical leak can be hazardous) and also safety issues (for example, leaking natural gas has an associated risk of explosion and/or ignition). Indirect implications are often concerned with loss of service provided by the pipeline and the impact of the loss of service to the served customers or systems.

One area where faults are relatively commonplace in pipelines is in water supply pipelines. Drinking water is commonly supplied under pressure via what is referred to as a water distribution main. Drinking water distribution networks commonly have a loop or branch network topology, or a combination of both, supplied by so-called "trunk mains". The piping networks are often circular or rectangular. If any one section of water distribution main fails or needs repair, that section can be isolated without disrupting all users on the network.

A catastrophic trunk main failure is capable of causing both immense damage and dislocation to the day to day operation of a water supply network. Alongside that, however, has to be balanced the risk of such an event occurring and the cost of mitigating the risks of such an event occurring.

As water mains are typically buried below ground, accessing them is complicated, expensive and disruptive. As a result, many utility companies operate reactively (fixing faults as they arise) rather than pro-actively replacing outdated pipelines (for example, many of London's drinking water mains are said to date back over 100 years). In addition to the sheer cost of replacement, it is difficult for utility companies to be pro-active when the potential fault is buried and out of sight. It can be some time before a fault is even identified.

Statement of Invention

According to an aspect of the present invention, there is provided a pipeline fault detection system comprising a vibro-acoustic sensor connectable to a fluid path of a pipeline and a remote monitoring system, the sensor being operable to measure one or more predetermined vibro-acoustic properties of the fluid and/or fluid path and communicate data on said measurements to the remote monitoring system, the remote monitoring system being arranged to monitor said data over time and being further arranged to screen the monitored data for characteristics representing a fault type to identify occurrence of a fault type in the pipeline.

The pipeline monitoring preferably further comprises a reference model encoding parameters on the pipeline under predetermined operating conditions, the remote monitoring system being arranged to screen the monitored data for said characteristics in dependence on the reference model.

The remote monitoring system is preferably arranged to screen the monitored data for characteristics present in the monitored data over time.

The pipeline fault detection system preferably further comprises a further vibro-acoustic sensor, the vibro-acoustic sensor and the further vibro-acoustic sensor being a sensor pair and encapsulating a section of the pipeline between them to measure one or more predetermined vibro-acoustic properties of the fluid and/or fluid path and communicate data on said measurements to the remote monitoring system.

The remote monitoring system may be arranged to perform signal correlation and filtering on data received from a sensor pair to screen for said characteristics.

The remote monitoring system may be arranged to estimate the velocity of acoustic waves propagating through the pipe in dependence on said received data from a sensor pair and on a measure of the distance along the pipeline that is between the sensors of the sensor pair.

The vibro-acoustic sensor may be mounted in a sensor head, the sensor head further comprising a geophone connected to a skin of the pipe and arranged to arranged to measure velocity of signals in the skin of the pipe and communicate data on said velocity of signals to the remote monitoring system.

The sensor head may further comprise a pressure sensor arranged to monitor fluid pressure and communicate data on said fluid pressure to the remote monitoring system.

The pipeline monitoring system may further comprise a flow meter arranged to communicate data on fluid flow in the pipeline to the remote monitoring system, wherein the remote monitoring system is arranged to monitor for bursts in the pipeline in dependence on data from the flow meter and on data on the fluid pressure.

The remote monitoring system may be arranged to monitor for transient events in dependence on rate of change of pressure measured by said pressure sensor.

The remote monitoring system may be arranged to cross check a detected transient event against any data received from a flow meter to exclude the transient event being a pipe burst event.

The remote monitoring system may be arranged to cause one or more of the sensors to perform a diagnostic test selected from the set including electronics tests; software tests; tests against a high precision voltage reference linked to the sensor; and tests between pairs of sensors in the pipeline one of the pair being a source of a test signal and the other being a test subject.

The pipeline fault detection system may further comprise a remote unit connected to the sensor via a data cable, the remote unit including a data communication system arranged to receive data on said measurements via said data cable from the sensor and arranged to communicate data on said measurements to the remote monitoring system.

The or each vibro-acoustic sensor may comprise a hydrophone.

At least selected ones of the sensors may perform measurements substantially continuously over at least a predetermined period and are arranged to collate data on said measurements and communicate said data to the remote monitoring system on a periodic basis.

Upon data of a predetermined characteristic being detected, the or each sensor may be arranged to communicate data on the predetermined characteristic with the remote monitoring system outside of the periodic basis.

According to another aspect of the present invention, there is provided a sensor head including a body connectable to a fluid path passing through a pipe of a pipeline, the sensor head including a hydrophone arranged to be in direct contact with fluid when the body is connected to the fluid path, the hydrophone being configured to measure one or more predetermined vibro-acoustic properties of the fluid and/or fluid path, the sensor head being arranged to communicate data on said measurements to a remote monitoring system.

The sensor head when connected to the fluid path is preferably also connected to a skin of the pipe, the sensor head further comprising a geophone arranged to measure velocity of signals in the skin of the pipe.

An accelerometer may be used in place of a geophone.

The sensor head may further comprise a pressure sensor.

The sensor head may further comprise a heating system configured to heat the sensor head.

According to another aspect of the present invention, there is provided a method of detecting fault events in a pipeline comprising:

measuring, using a vibro-acoustic sensor connected to a pipeline having a fluid moving in a fluid path, one or more predetermined vibro-acoustic properties of the fluid and/or fluid path;

communicating data on said measurements to a remote monitoring system;

monitoring said data over time;

screening the monitored data for characteristics representing a fault type to identify occurrence of a fault event in the pipeline.

The method may further comprise predicting the occurrence of a future fault event in dependence on the monitored data.

The method may further comprise causing preventative maintenance on the pipeline in dependence on said predicted occurrence of a future fault event.

Embodiments of the present invention seek to provide a pipeline fault detection system comprising a sensor head connectable to a fluid path of a pipeline and a remote monitoring system, the sensor head being operable to measure one or more predetermined properties of the fluid and/or fluid path and communicate data on said measurements to the remote monitoring system, the remote monitoring system being arranged to monitor said data over time and being further arranged to screen the monitored data for characteristics representing a fault type to identify occurrence of a fault type in the pipeline.

Preferably, a pair of sensor heads are used, encapsulating a section of the pipeline between them.

Embodiments of the present invention enable continuous monitoring of pipelines to detect occurrences of faults and also characteristics associated with impending faults. As such, pro-active monitoring and maintenance can be performed: avoiding the cost of total replacement of pipeline sections; avoiding the impact on customers of total replacement; extending pipeline operating lifetimes;

reducing human inspection/replacement activities and thereby avoiding the detailed health and safety requirements and complexities of contamination avoidance and traffic disruption; and enhancing resource allocation (work can be prioritised based on actual/predicted fault type);

avoiding pressure drops, clouding and transients;

long-term planning, confidence and performance sustainability;

asset condition and lifetime assessments are based on real-time monitoring rather than assumptions. This can allow decision-making to be changed from probability/assumption based to an informed basis.

Permits decisions on asset replacement to be based on real-time information and risk-mitigation (rather than assumed lifetime and invasive coupon testing), so facilitating enhanced targeting of infrastructure replacement spend, reduced invasive testing and stretching of asset replacement timetables;

an extension of trunk main asset lifetime, based on informed on-going analysis rather than assumptions as to condition, so permitting total lifetime asset costs to be spread over an extended period with per year asset cost consequently reduced;

a reduction in substantial insurance claims and ostensible mitigation of the causes of potential major claims;

the avoidance of "critical incident" events requiring the calling in of standby teams, at an operational and management level, the re-routing of supplies, significantly increased call centre volumes, as well as compensation;

the transformation of emergency repairs into scheduled repairs; and the avoidance of repeated expenditure on periodic inspections requiring potentially extensive traffic management and repeated contamination risk.

Embodiments of the present invention enable remote monitoring of actual conditions in a pipeline without needing engineers at the pipeline. As such, a more complete understanding of monitored pipelines can be achieved and monitoring can be substantially automated and used to trigger alerts via mechanisms such as SMS, email, web and/or SCADA.

In a preferred embodiment, a sensor head includes a body connectable to a fluid path of a pipeline, the sensor head including a hydrophone arranged to be in direct contact with fluid when the body is connected to the fluid path Immediate burst notification may also be incorporated by inclusion of a flow meter. Pressure transient detection may also be performed.

The remote monitoring system uses a modelling system which understands the 'normal' operating conditions for the pipe in a variety of environmental conditions and times of day. Unusual events are identified and calculations applied to identify if a leak or other fault exists. By taking data from multiple sensors heads mounted directly on the pipe in the fluid path, the remote monitoring system is also able to locate the detected leaks/failures. As a result of that early location and detection, small leaks can be repaired in a planned manner and catastrophic failures and consequent interruption of supply are avoided.

Preferred embodiments enable hi-resolution, online, real-time monitoring of properties of fluid/fluid path such as pressure, flow and other parameters. The sensor heads may also be configured to provide data suitable for pressure transient tracking and analysis.

Preferred embodiments of the present invention use a mixture of vibro-acoustic signals, present in the water in the pipe and in the skin of the pipe and generated by the fluid escaping under pressure. Such an arrangement enables monitoring pipelines over distances of about 1 km (0.6 miles) with an accuracy of about 2 m.

In contrast to solutions that seek to utilise ultrasonic flow meters to infer detection of leaks, embodiments of the present invention utilise sensor arrangements that enable direct detection of fault and leak events.

Pumps, turbulence, changes in geographic height and take-offs (side branches) all affect pressure. At any scale of measurement, pressure modulation can be seen, at different time and pressure scales. This modulation will also be imprinted on any measurement of speed of flow of fluid making determination of the cause of a change in fluid flow speed difficult. Such methods are therefore only suitable on pipelines where conditions are very favourable; long, straight and relatively flat with no side branches, for example.

Embodiments of the present invention are not so limited and are able to cope with complex pipeline geometries, having safe-guards in place so that take-offs are not incorrectly identified as leaks.

BRIEF DESCRIPTION OF THE DRAWING FIGURES

Figure 5A:
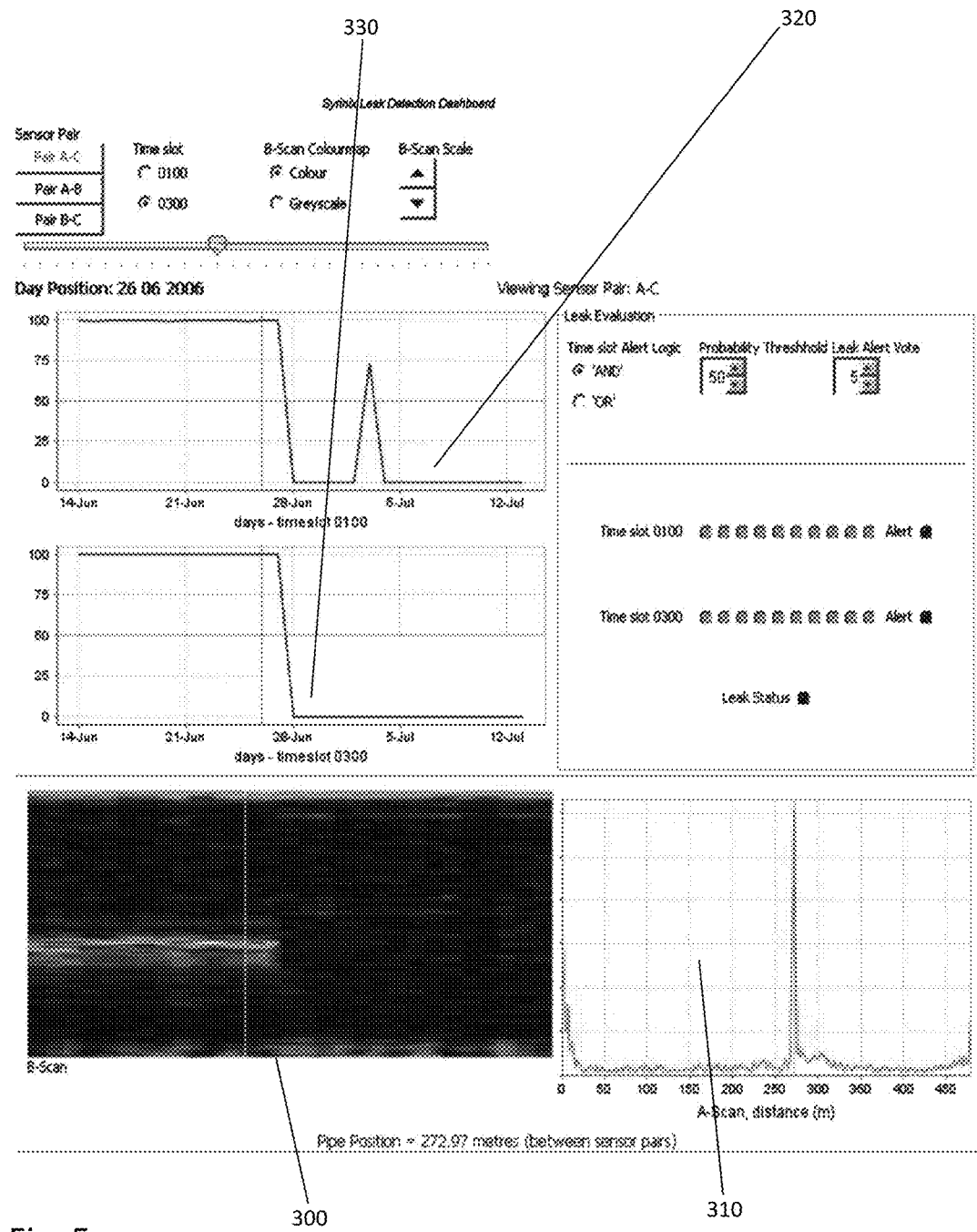
Figure 5B:
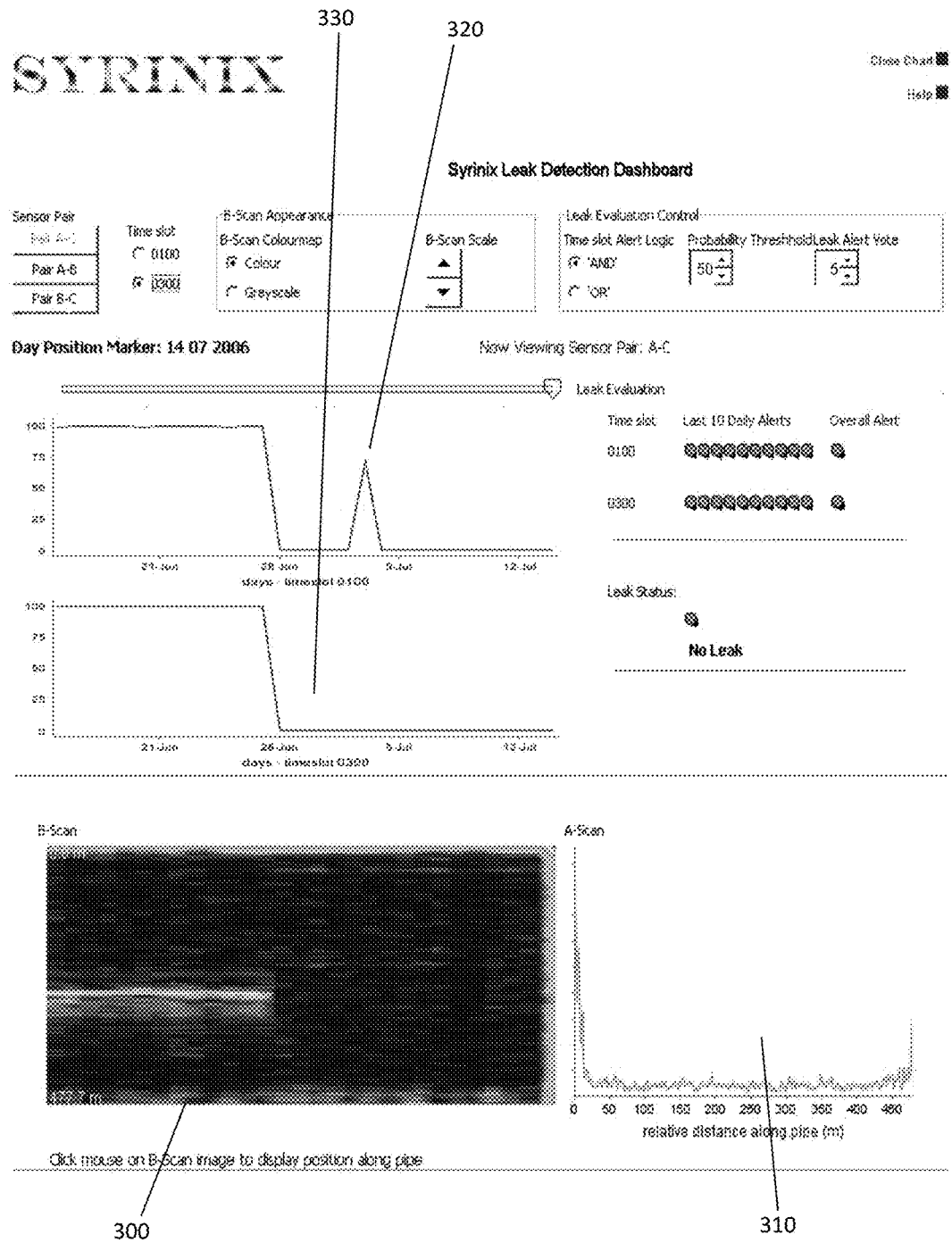

FIGS. 5*a* and 5*b* are visualisations of A-Scan and B-Scan (2D A-Scan plots).

Figure 6:
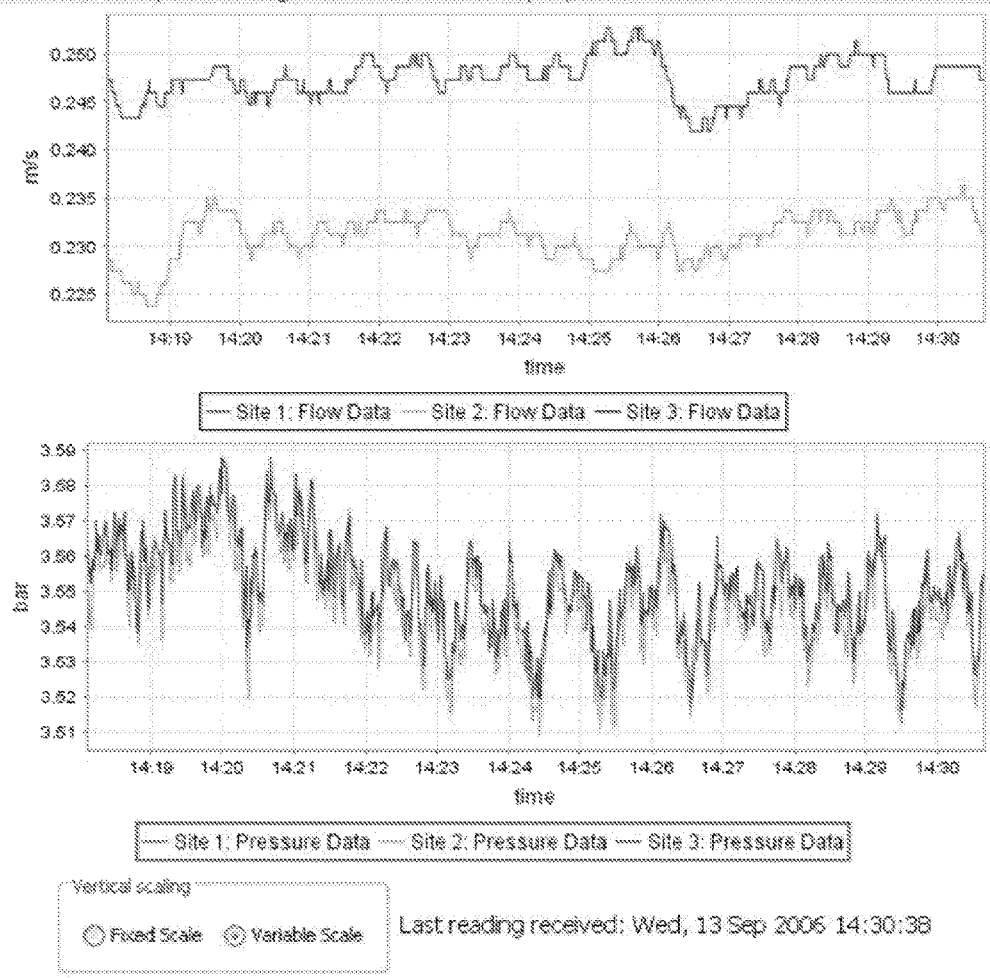

FIG. 6 shows an example view of real-time pressure/flow charting.

Figure 7:
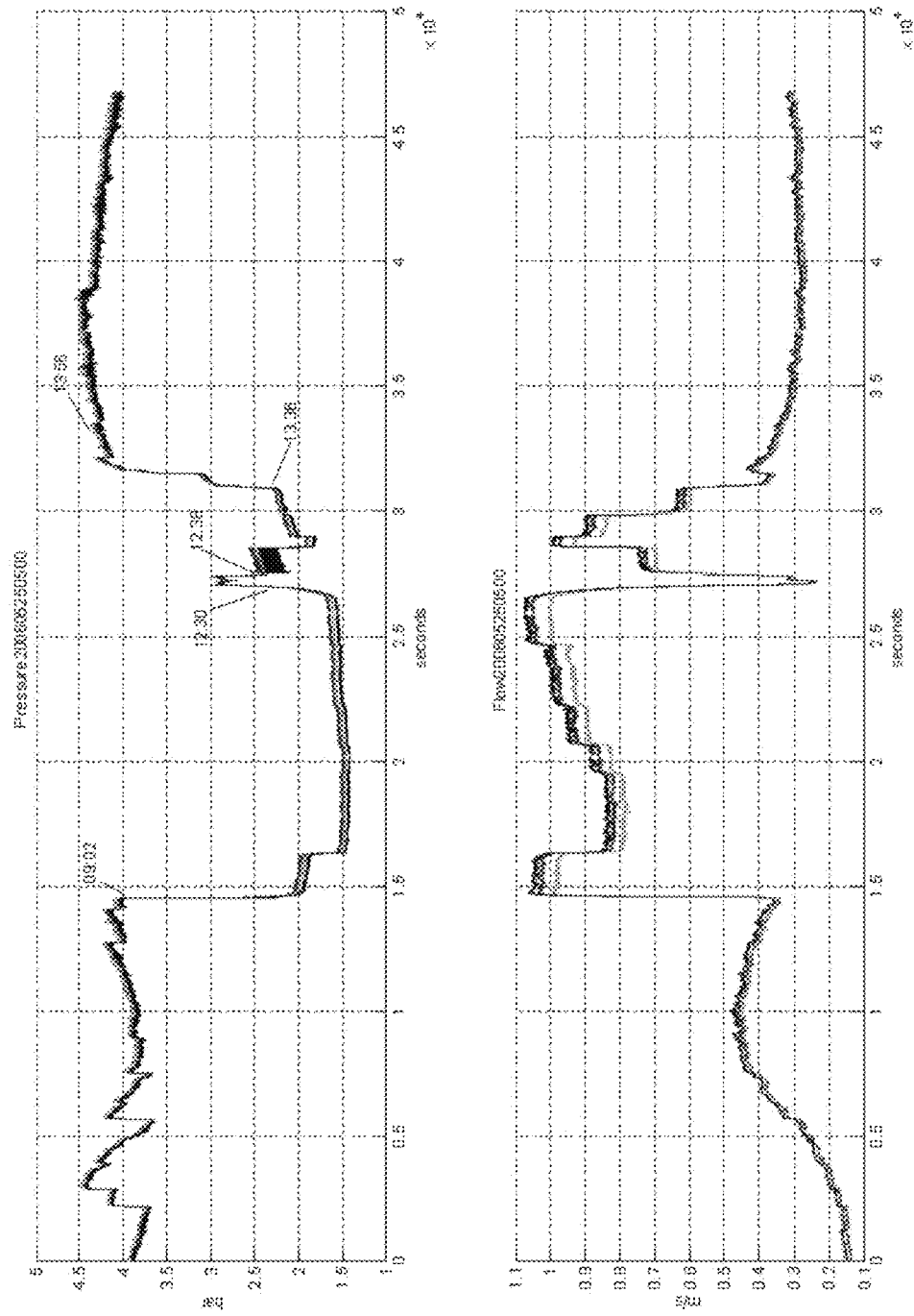

FIG. 7 illustrates certain burst events.

Figure 8:
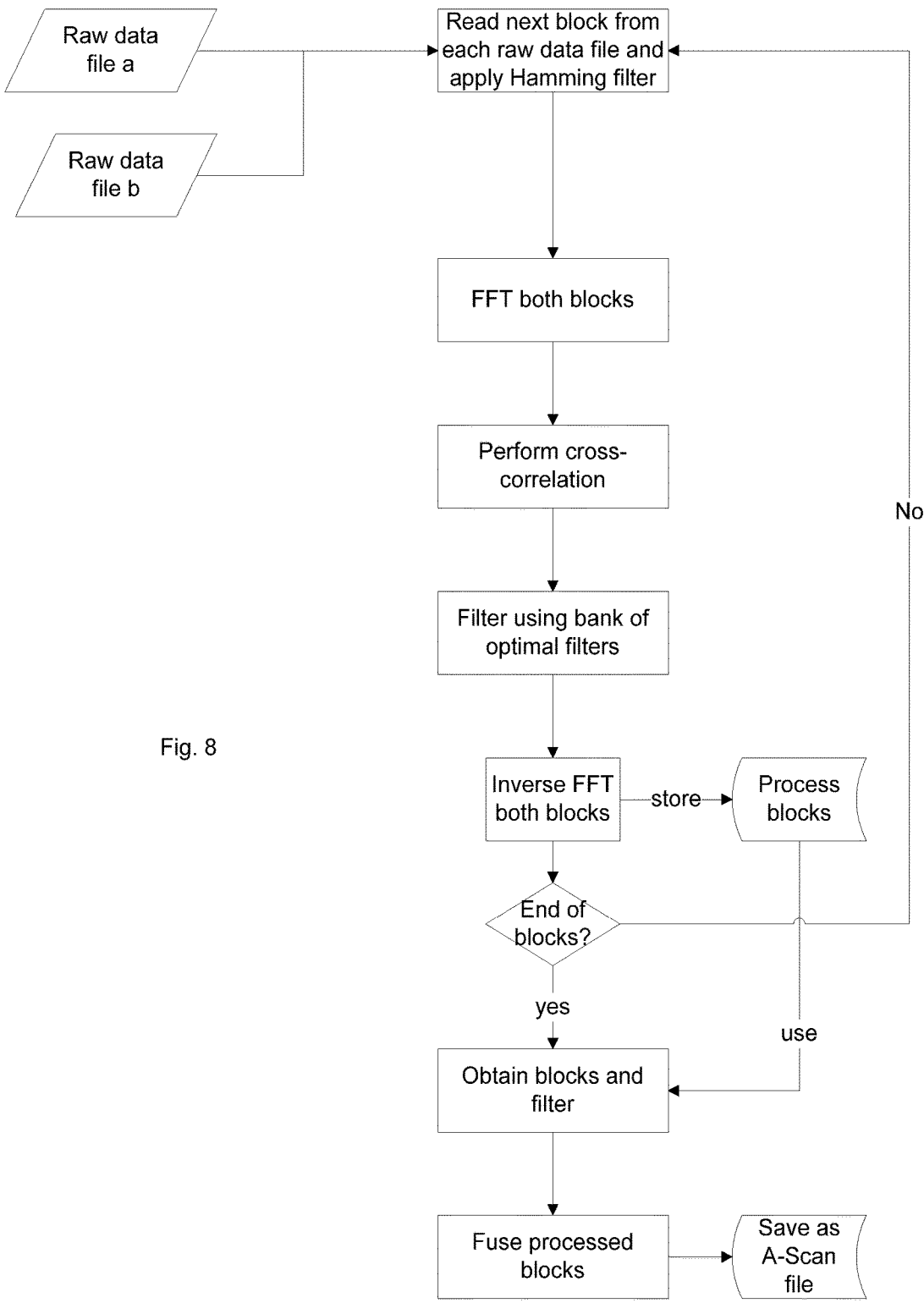

FIG. 8 illustrates a flow diagram for generation of an A-Scan file according to an embodiment of the present invention.

Figure 9:
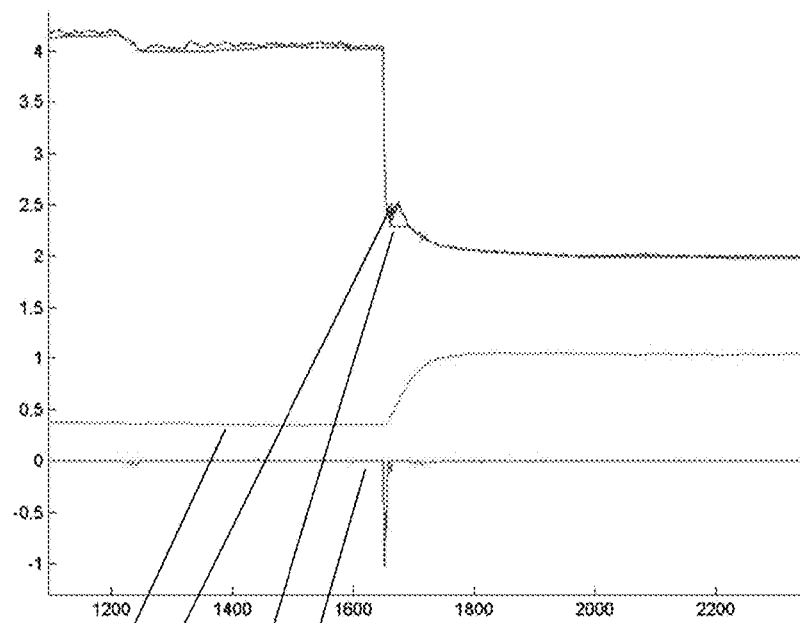

FIG. 9 illustrates certain burst events.

Figure 10:
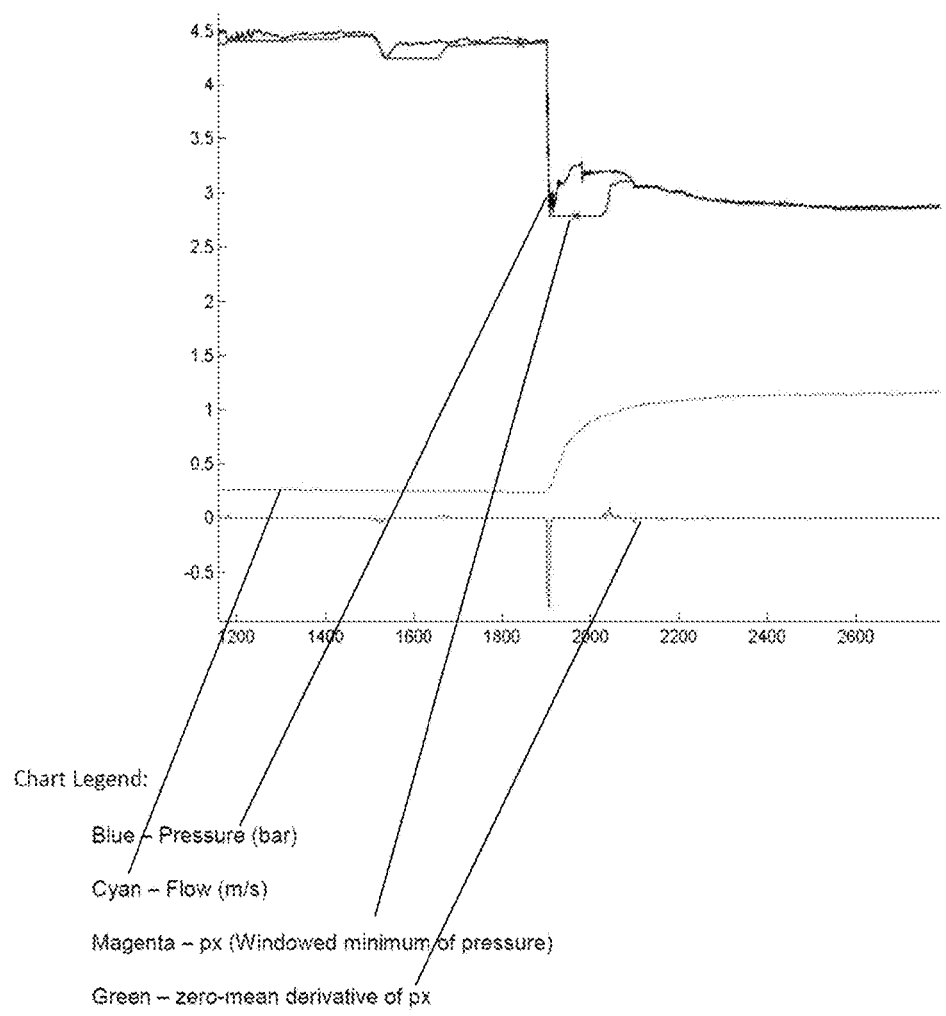

FIG. 10 illustrates certain burst events.

DETAILED DESCRIPTION

Figure 1:
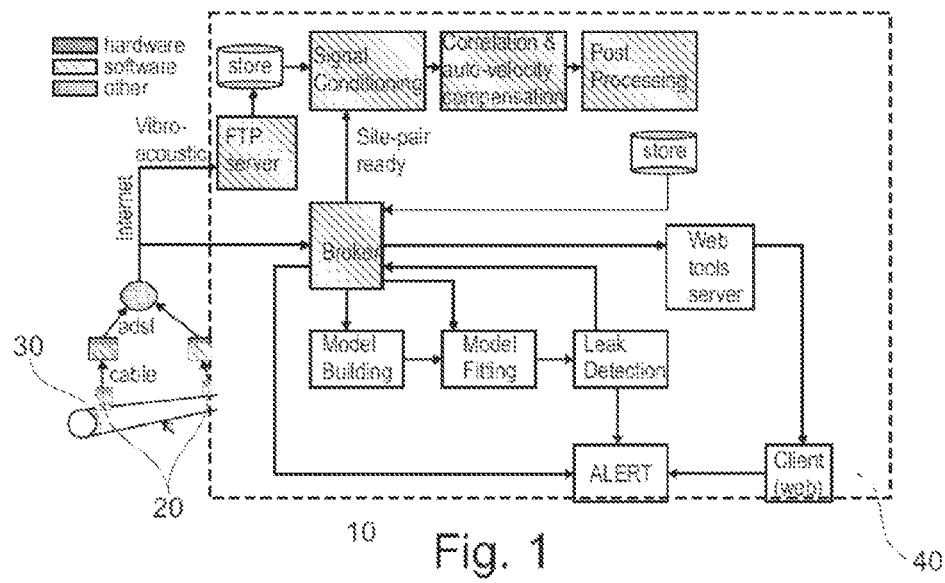
FIG. 1 is a schematic diagram of a pipeline fault detection system according to an embodiment of the present invention.

FIG. 1 is a schematic diagram of a pipeline fault detection system according to an embodiment of the present invention.

The system 10 includes a sensor head 20 connectable to a fluid path of a pipeline 30 and a remote monitoring system 40, the sensor head 20 being operable to measure one or more predetermined properties of the fluid and/or fluid path and communicate data on said measurements to the remote monitoring system 40, the remote monitoring system being arranged to monitor said data over time and being further arranged to screen the monitored data for predetermined characteristics representing a fault type to identify occurrence of a fault type in the pipeline.

The remote monitoring system 40 preferably monitors emergent leaks for a relatively long period (which can be varied according to client requirements) before raising an alert. This approach, only practical in a completely automated system, allows alarms to be raised with a high degree of confidence and substantially eliminate false positives.

In preferred embodiments, data received from pairs of sensor heads 20 is processed to produce what is referred to as an A-file. The A-Scan file is a filtered and refined representation of aspects of the pipeline and indicates a measure of fault-like signals that exist along the section of pipe being monitored between the pair of sensor heads. It will be appreciated that a sensor head could potentially be a member of more than one "pair" as it may be upstream of one sensor head and downstream of another.

Alerts can be provided via normal system control systems, such as the OPC SCADA protocol, or automated SMS messaging, as well as operating statistics and graphics via a 'dashboard' computer interface such as via a website. Screens of such an interface are shown in FIGS. 5*a*, 5*b*, 6 and 7.

It will be appreciated that the pipeline leak detection system is not limited to particular pipeline types, pipe materials or fluid types. For example, the sensor head could be mounted in various pipe types including cast iron, steel, concrete, MDPE and PVC.

Leak detection resolution is typically accurate to around 1 meter but depends on number of sensor heads used, site characteristics and pipe material.

Preferably, up to 5000 readings per second are taken by sensors in the sensor head 20. In the case of pressure and flow monitoring, around 25 readings per second are provided to the remote monitoring system 40.

Figure 2:
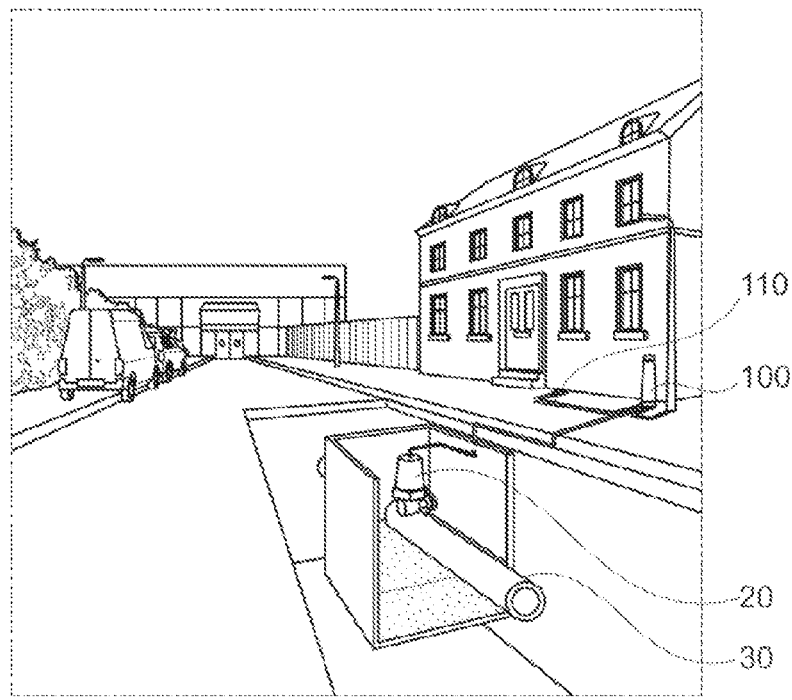
FIG. 2 illustrates a sensor head connected to a roadside/street level unit according to an embodiment of the present invention.

Communication between a sensor head and the remote monitoring system can be achieved in many ways including wired and wireless telecommunication networks. In a preferred embodiment, illustrated in FIG. 2, the sensor head is connected to a roadside/street level unit 100 that is in turn connected to an ADSL enabled telephone line 110 such that measurements can be communicated via VPN or another secure means using the ADSL line to connect to the remote monitoring system 40.

Figure 3:
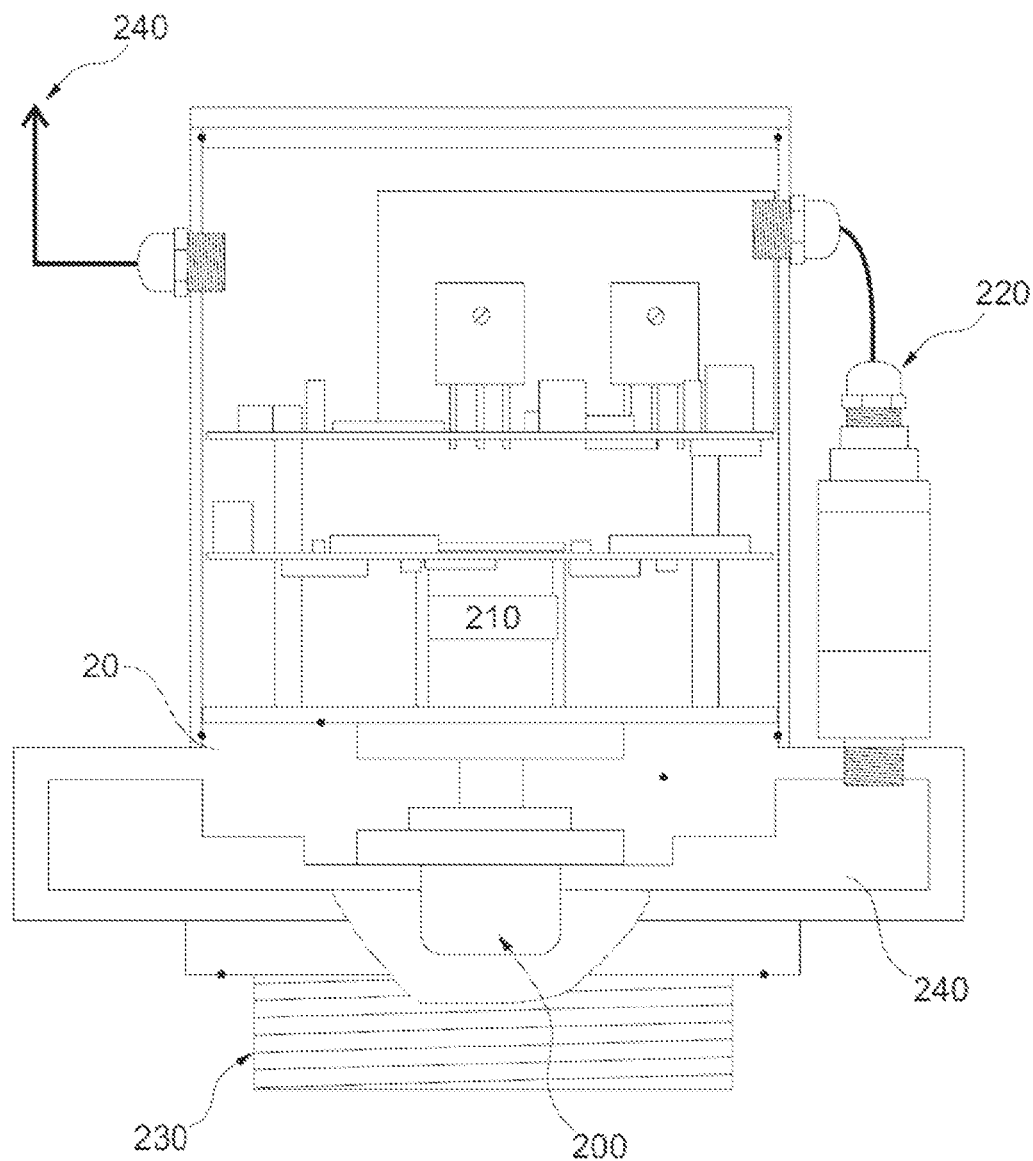
FIG. 3 is a sectional diagram of a sensor head according to an embodiment of the present invention.

FIG. 3 is a sectional diagram of a sensor head 20 according to an embodiment of the present invention.

Preferably, there are three sensors in the head 20: a hydrophone 200; a geophone 210; and a pressure sensor 220.

The sensor head is connected to a pipeline via a valve connector 230. A valve on a pipe is opened and the screw thread of the valve connector mates with a corresponding thread in the valve (although it will be appreciated that other mating arrangements could be used).

The hydrophone 200 is arranged to be in contact with the fluid when the sensor head is connected and fluid is running through the pipeline. The sensor head 20 includes an internal pressure vessel area 240 into which the pressure sensor 220 is fitted, on the right, as well as the area where the hydrophone 200 is mounted.

In operation, vibro-acoustic signals are acquired by the hydrophone 200. The range of signals experienced can be extremely wide as sites vary and may have differing characteristics. The sensor head preferably includes circuitry to enable varying of the sensitivity and the frequency response either by direct configuration at the sensor head, at the roadside unit or via remote commands from the remote monitoring system 40.

Preferably, the frequency response for the hydrophone extends from about 1 Hz to about 2500 Hz.

For certain faults and conditions, the skin of the pipe is monitored in addition or as an alternative to monitoring of fluid conditions/properties. The geophone 210 is arranged to measure velocity of signals in the skin of the pipe. The geophone is used in preference to an accelerometer due to improved sensitivity in large diameter pipelines. The frequency response for the Geophone extends from about 8 Hz to about 400 Hz.

In operation, the leak detection system is monitoring for signals that are extremely small and orders of magnitude smaller than the "noises" in the main—caused by the flow, bubbles, external environmental noise (such as traffic, aircraft, road-works etc). However, a leak has characteristics that are detectable in the received signals and are present and always in the same place. The noise/signals from uncorrelated, or short-time correlated sources, such as traffic, present themselves, in the signal processing scheme, as features in the A-scan which are very short lived and which move in position. A leak, on the other hand, presents a feature in the A-scan which is in a fixed position and is always present. Even though it may have a magnitude which is smaller than the other sources, this consistency is a characteristic that can be exploited by the detector. In this case this characteristic is exploited by the presence of the detection system for long periods of time (because it is permanently installed), an opportunity not available to previous leak detectors.

True leak signals also have a characteristic signature in the spectrum of frequencies that they cover. Whilst this signature differs from one site to another, at any particular site they are consistent over long periods of time and hence filtering can be deployed to maximise the acquisition of this wanted signal compared to the unwanted noise.

Using the Hydrophone and Geophone this "leak noise signal" is acquired, along with all unwanted noise, and passed through the roadside unit 100 to the remote monitoring system 40 for processing alongside data from other sensor heads.

When a burst occurs, a huge pressure wave propagates along the pipe. The pressure sensor in the sensor head 20 detects the pressure wave (in addition to being able to provide data for more on-going pipeline network management tasks such as management of fluid pressure supply). If an optional flow meter is present, information about the flow is combined at the remote monitoring system 40 with the pressure data to make a decision about the burst; is it actually a burst and not some other event such as pump failure; in which direction, relative to the sensor head, is the burst.

The pressure sensor is sampled at the base rate of the system (which is in this embodiment 5 kHz but could be set at other values) but this is not a sensible reporting rate. The pressure reading is therefore down-sampled to 25 readings per second but both rates are available for pressure transient detection. In a standard configuration this is the rate at which sensor heads report pressure in real-time to the remote system 40 but higher rates are easily achievable should they be needed.

The sensor heads acquire vibro-acoustic signals from the trunk main on a continuous basis at a high sample rate. These measurements can be processed to give a "noise level" for the pipeline and fluid flow.

Sensor heads can be triggered from the remote monitoring system to perform diagnostics tests on both electronic and software components which can be run remotely. For example, a sensor head may include a high precision voltage reference that can be switched in to enable testing of electronics and measurement devices. In one embodiment, a signal may be induced in a pipe or fluid travelling in a pipe for detection at a sensor head downstream (or upstream). For example, a hydrophone of one sensor head could be driven to generate a signal to be detected at another sensor head.

Preferably, the street level unit 100 includes power and communication components necessary for local sensor heads to operate and communicate with the remote monitoring system 40. A single street level unit may support multiple local sensor heads. The street level unit may preferably include a GPS based time reference system and associated GPS antenna. The time reference system is used to provide a timestamp to data measurements obtained from the sensor head prior to transmission to the remote monitoring system 40. It will be appreciated that timing accuracy is helpful to the remote monitoring system and avoids any issues such as latency that may arise during transmission to the remote monitoring system 40. It also means that measurements from different sensor heads can be more accurately compared or combined. It will be appreciated that other time reference systems could be used such as local clock or some network based clocking signal.

Alongside the sensor head installation on the pipeline, one embodiment mounts a street level unit and flow meter in a small kiosk or bollard (though only one flow-meter is required for individual stretches of monitored main).

The sensor head, which is installed on the main being monitored, is suitable for continuous submersion. The sensor head may be a low voltage system, transformer isolated from the mains voltage supply and may be a SELV system. The low voltage supply from the street level unit to the sensor head is preferably fuse protected.

Preferably, the street level unit and/or the sensor head include a power regulation system so as to lower the electronic noise floor which translates into improved sensor performance.

Power is preferably released as heat within the sensor head. While this at first seems a contrary step when the focus today is on lower over-all power consumption, reliability and longevity in the cold, wet environment in which the sensor head is placed is improved due to internal warming deliberately introduced into the sensor head.

In one embodiment, the street level unit can be pre-installed and configured into the top section of the bollard; the bottom section of the bollard being issued to the civil engineering crew responsible for the installation site. Fitting is then a case of arriving at the site and attaching the pre-configured top half.

As an alternative to a street level unit, the respective components could be installed in an underground chamber.

At the site to be monitored, two or more sensor heads are preferably fixed to tappings on the same trunk main with a separation which may typically vary between 200 to 1000 m. The area of trunk main protected by the system lies between sensors. Generally speaking, the closer the sensors are to one another the more sensitive the system will be for detecting leaks. It will be appreciated that certain types of monitoring (including burst and transient) do not require multiple spaced apart sensor heads and could be accomplished with a single sensor head. Indeed, even leak detection can be accomplished with a limited degree of accuracy with a single sensor head. It will also be appreciated that pipelines other than trunk mains can be monitored in the same manner.

The sensor heads are each connected, via an umbilical cable 240, to a processing unit in the street level unit, which is usually housed in a plastic bollard or other roadside furniture. The processing unit comprises a computer system which handles the collection and broadcast of sensor data, an ADSL modem and power supply. Most installations will be provided with mains electricity and ADSL internet. As an alternative to ADSL, a cellular network or other communication network may instead be used to communicate with the remote monitoring system 40. Power supplies other than mains power could be used such as solar power, battery or energy scavenging technologies.

As previously discussed, the sensor heads continuously collect data at a high sampling rate of about 5 KHz. This, along with internet connectivity, enables pipe infrastructure to be monitored and observed in real-time.

The tasks performed by the sensor head and street level unit include:

Continuous acquisition of multi-channel sensor data from the sensors;

Nightly or periodic collections and upload of data to the remote monitoring system for leak detector data;

Monitoring of pressure and flow (if meter installed) for Burst detection;

Broadcast of pressure and flow values at resolution of 25 Hz.

Large recordings of data are taken during a period (typically overnight) when the ambient noise is at its lowest. This data is then uploaded, preferably via FTP, to the remote monitoring system 40 to be used by the leak detection process. Other data such as live pressure and flow readings, alarms and general system status are published from the sensor system preferably via the MQTT messaging broker.

The remote monitoring system 40 performs fault detection signal processing. In one embodiment, fault detection is correlation based and data from a pair of sensors is used for performing the correlation. The fault detection application running at the remote monitoring system preferably continuously searches for new, unprocessed data as it is received or uploaded. Any new file sets are processed immediately upon discovery and made available for user interaction.

Periodically, the fault probability data is checked by the system. Based on user defined logic for each site pair configuration, fault alarms are generated. As it is permanently installed, an embodiment of the present invention can build up a long view of pipeline fault probability. A single day snap-shot of analysis is simply not robust enough to base operational decisions.

A leak-like signal may be present due to a temporary noise event being present at the time of recording. By building up a picture of fault-like noise activity over several days more confident decisions can be made. The data can also be viewed back several months or years, enabling gradual changes in a pipe's characteristic to be observed.

The fault detection processing takes place at the remote monitoring system 40. Burst detection may optionally be performed locally at a sensor head. In preferred embodiments, the sensor head and street level unit contains no information regarding the fault detection process. The sensor head and street level units in a preferred embodiment essentially collect raw sensor data and upload it to the remote monitoring system.

Once uploaded data for a specified site pair (of sensors) has been received, the following steps are performed at the remote monitoring system:

1. Data preparation and validation
2. A-Scan generation
3. Fault probability evaluation Following the successful completion of the above steps data for the site pair in question is generated. In a preferred embodiment the data includes an A-Scan file and a fault probability value. The A-Scan file is a filtered and refined representation of aspects of the pipeline and indicates a measure of fault-like signals that exist along the section of pipe being monitored. The file is generated from readings received from the hydrophone and geophone that are subject to a combination of signal correlation and filtering. The fault probability value is evaluated using the A-Scan and predetermined models of fault-like and non-fault-like pipe behaviour. It is a value of between 0-100%, where 100% represents high fault probability.

In one embodiment, processing generates a separate A-Scan for both the Geophone and Hydrophone extracted data sets.

The raw source files typically will contain interleaved data from all the sensing systems data channels. Since channel identifiers exist in the data some channels may have been excluded from the raw file when it was written on site to reduce file size. These files are reconstructed during verification, to ensure consistency.

The data sets returned to the remote monitoring system have embedded diagnostic codes and checksums to enable the signal processing system to verify the integrity of the data. The data preparation and verification step ensures that there have been no errors in transmission and, more importantly, no errors in the data collection at the road-side by the sensor head. Preferably a data-rate optimisation and coding step has preceded transmission to minimize the telemetry bandwidth and hence the data will have to be decoded before processing.

The generation of an A-Scan file is illustrated in FIG. 8 and includes:

1) Initialisation (Read raw files, create processing structures)
2) Create A-Scan
3) Estimate Velocity (of acoustic sound wave through pipe)

If velocity estimate differs from default value then re-create A-Scan using new value 4) Auto-alignment of A-Scan out-of-bracket peaks
5) Generate A-Scan histogram feature
6) Write A-Scan to file The term "bracket" refers to the section of pipe being monitored between a pair of sensor heads. Out of bracket peaks are peaks originating from outside of the section being monitored.

Due to their size, data sets are preferably block-processed to generate the A-Scan. The number of blocks used depends on the length of the data set (sensor recording) and the block length selected (typically 65536 samples). Each block pair is processed with a cross-correlation function, performed in the frequency domain for speed. The block then undergoes a process of filtering to bring out any leak noise information that may be present. At the cross-correlation stage the plot is generally overwhelmed by the noise baseline in the raw data. Optimal filters with different centre frequencies are used to filter each processed block. Once all the blocks within the full data set have been processed they are filtered and fused (combined) into a single A-Scan file.

Following step 2 above, the application attempts to estimate the velocity of acoustic waves propagating through the pipe (Step 3). The velocity estimate uses the sensor pair separation distance, the position of the A-Scan out-of-bracket peaks (located at either end of the A-Scan plot), and the original velocity estimate to calculate a velocity adjustment value. By increasing the accuracy of the velocity estimate the accuracy of leak location is improved.

The auto-alignment step (Step 4) rescales the A-Scan plot between the two peaks that are present at either end of the plot due to the effect of out-of-bracket noise. By doing this the accuracy of pin-pointing the leak location is improved.

The histogram feature is used as the input to the leak probability modeller. The A-Scan from this point on serves as a visual tool for user interaction with the data. The histogram is directly built on A-Scan values and is then normalised.

Figure 4:
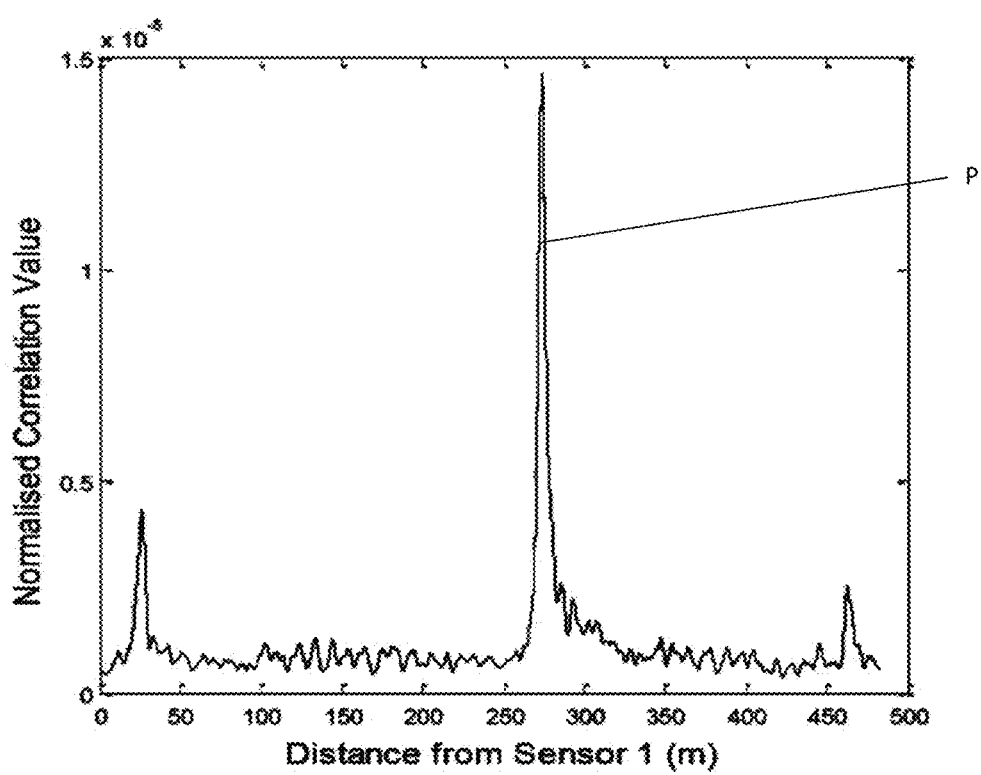
FIG. 4 shows an example A-Scan plot for a pipe with a leak.

An example A-Scan plot for a pipe with a leak is shown in FIG. 4. The large peak labelled "P" close to the centre indicates the leak location. The out-of-bracket peaks are also shown in this plot as an exemplar although normally they are removed by the alignment process. An A-Scan for a pipe with no leak signal would resemble noise as the noise floor is lifted by the absence of the large peak.

The correlation function generated from signals on a pipe with a leak tends to have a single large peak at the leak position. In contrast, functions generated by signals from a pipe in which there is no leak tend to have multiple small peaks of similar amplitude. The shape of the processed correlation function is therefore a sensitive indicator of developing leaks, and hence a good feature for use in the signature checker.

The leak probability is calculated based on a distance measure between the histogram generated from the A-Scan and sample histograms based on leak and no-leak pipe scenarios.

The sample histograms are generated from either real data or generic simulated data. The disadvantage of using real data histograms is that the data required to create them must be collected under known pipe conditions and the leak data case is particularly problematic. Generic models have been shown to perform well.

The histograms contain 32 bins, or values, representing the number of occurrences of A-Scan samples at each of the 32 levels. The leak probability is evaluated as the mean squared distance along each dimension and exponating.

$$Pr(X \mid M) = e^{-\frac{1}{N}\Sigma_i \frac{(x_i - \mu_i)^2}{2\sigma_i^2}}$$

This definition returns unity for the mean vector of the model and lower values for all other vectors. Therefore it is used to generate two probability values: one for the histogram using the leak model (Pleak) and another for the non-leak model (Pnoleak). The overall leak probability expressed as a percentage is evaluated by:

$$P = 100 * \frac{\exp(P_{noleak} - P_{leak})}{(1 + \exp(P_{noleak} - P_{leak}))}$$

The data generated by the leak detection process can be visualised for each sensor site pair in the customer's network. The visualisations include leak probability values plotted back through time aligned to a 2D representation of the A-Scans, called the B-Scan. The B-Scan is an interpolated stack of A-Scan plots which produce a novel image of pipe leak signal activity. Trails can be observed running through the B-Scan corresponding to leak. It is clearly visible when the leak in that particular pipe was fixed as the leak trail in the B-Scan stops. These visualisations are shown in FIGS. 5a and 5b with the B-scan illustrated as item 300, the A-scan as 310 and items 320 and 330 illustrating leak probabilities at different times (high values indicating likely leak).

The burst detection algorithm preferably uses both pressure sensor data and flow meter data. However, burst events could be detected using pressure sensor data alone.

Initially only considering the pressure signal a burst event lies between a pressure transients and a pumping variation in terms of duration of pressure change. Transients are short, sub-second to a few seconds. Pumping variations occur slowly, so as to not damage the infrastructure, typically several minutes. A burst event appears to occur over several seconds and is always a drop in pressure. The magnitude of the drop is significant, often several bar as the pipe equalizes to atmospheric pressure. The flow meter reading would quickly rise if the burst were downstream from the sensor or fall if upstream. Burst events can be robustly determined by monitoring both pressure and flow. A significant pressure drop, within a specified time interval coupled with a significant variation in flow indicates a burst, or some other serious event, has occurred.

The burst detection algorithm is passed time-aligned pressure and flow data which has been down sampled to a 1 Hz resolution. Therefore the function window length FN_WINDOW of 120 samples represents 120 seconds.

| | | |
|---|---|---|
| FN_WINDOW | 120 | The number of samples in the function window |
| STEP_INT | 3 | The step detect interval |
| PRES_TRIG | 0.5 | The negative pressure slope trigger |
| PRES_MIN | 1 | The minimum drop in pressure required to trigger an alarm |
| WIND_PAD | 60 | Window padding |
| MIN_LEN | 3 | The minimum slope sample width for classification as a burst event (to eliminate transients) |
| MAX_LEN | 140 | The maximum slope sample width for classification as a burst event (to eliminate pumping variations) |
| FLOW_VAR | 0.2 | The minimum change in the flow rate during the pressure drop for a burst event to be raised |

A sliding window processes the most recent FN_WINDOW samples.

A minimum of the last FN_WINDOW pressure samples is evaluated. A derivative is then taken using:

$$f(x)=f(x)-f(x-\text{STEP\_INT})$$

Use of the minimum instead of a mean assists in detecting rapid pressure descents.

A mean value of the last FN_WINDOW flow samples is evaluated. Then a derivative taken as above.

Check for Negative Pressure Gradients Steeper than the Pressure Trigger

The pressure trigger PRES_TRIG defines the threshold to search for negative pressure gradients within the pressure derivative data set. If a trigger occurs this does not mean that a burst has been found. Prior to a burst alarm the actual pressure drop has to be identified along with the variation in flow. Pressure and flow values are recorded at the index: current index−WIND_PAD A descent count is initiated to track the length of the pressure descent. In order for the pressure drop to trigger a burst alarm the descent must lie in the range MIN_LEN to MAX_LEN (seconds). If the descent is out of range it is disregarded and the counters/flags are reset.

Check for Alert

Once the window has passed the negative pressure gradient trigger point i.e. the gradient is less than the trigger, the index value is stored. Once the current index reaches the stored index plus WIND_PAD then the pressure and flow values are recorded. Now it is just a matter of checking the pressure drop exceeds PRES_MIN and the flow variation is greater than FLOW_VAR x the initial flow value.

FIGS. 7, 9 and 10 are illustrations of burst events.

Transient detection may also be performed by an algorithm that is a derivative of that given for the burst detector. A transient pressure event typically takes place over a shorter time and exemplar time windows for transient detection range from 10 seconds to 60 seconds. It is possible, and is in fact usually the case, that more than one time-window may be running in parallel in any particular detector.

The transient detector is only concerned with the rate of change of the pressure signal and the magnitude of the change, flow is not considered. However, unlike burst detection, the transient detector is concerned with both positive and negative gradients.

If a flow meter is present in the system, then once it is determined with a predetermined probability that a transient is detected, reference is made to the flow value to double check that a burst is not a possible candidate. Assuming this test is passed, the transient is marked as detected and an alarm raised if needed. Preferably, data from five minutes before the transient to five minutes after the transient is kept and tagged to associate it with this transient event. This captured data segment is used for further post event analysis and to form a library of transient events.

If a leak alarm is raised, or a burst or transient alert arrives from a sensor system the server will alert customers based on their configuration settings for the pertinent pipe. Options include SMS text messages and emails for alerts.

A SCADA bridge may also be used, offering data such as sensor site configuration, leak/burst alarms and system health can be made visible to a customer's SCADA system.

In one embodiment, communication between street level units and the remote monitoring system is handled using a publish/subscribe methodology called MQTT (Message Queue Telemetry Transport).

MQTT has the advantage it is portable so will run on all systems with ease and is small, which is advantageous for the sensor system computer.

The heart of MQTT is a broker to which clients connect. The broker runs on a remote server and client libraries are called from software applications. Clients subscribe to and publish to topics.

In addition to the core systems, several web-based tools have been developed. These are Java Applet files which run in web browsers and are accessed through a secure login area on a website.

The tools comprise:

Live Pressure/Flow Charting

Select sensor sites in the customer's network and view live pressure and flow data as it is published from the sensor. The resolution can be varied up to 25 Hz and plots can be zoomed.

Historic Pressure/Flow Charting

Browse archived Pressure/Flow data for any sensor site in the customer's network. Date/time range can be selected at various resolutions to view all data collected since the site was commissioned.

The invention claimed is:

1. A trunk mains pipeline fault detection system comprising a vibro-acoustic sensor connectable to a fluid path of a trunk mains pipeline and a remote monitoring system, the sensor being operable to measure, for a plurality of days and for a predetermined time period each day, the predetermined time period being less than 24 hours, one or more predetermined vibro-acoustic properties of the fluid and/or fluid path of the trunk mains pipeline when the trunk mains pipeline is online and under normal operating conditions so as to avoid interruption of a supply of water through the trunk mains pipeline and communicate data on each day's measurements to the remote monitoring system, the remote monitoring system being arranged to monitor said data over time to build a representation of gradual changes in said pipeline's characteristics from the monitored data over said plurality of days and being further arranged to screen one or more of the representation and the monitored data for characteristics representing a fault type to identify occurrence of a fault type in the pipeline, wherein the representation of gradual changes in said pipeline's characteristics built from the monitored data over said plurality of days is a function of the monitored data from the predetermined time periods each being less than 24 hours.

2. The pipeline fault detection system of claim 1, further comprising a reference model encoding parameters on the pipeline under operating conditions which avoid interruption of the supply of water through the trunk mains pipeline, the remote monitoring system being arranged to screen the monitored data for said characteristics of a fault type in dependence on the reference model.

3. The pipeline fault detection system of claim 1, further comprising a further vibro-acoustic sensor, the vibro-acoustic sensor and the further vibro-acoustic sensor being a sensor pair and encapsulating a section of the pipeline between them to measure one or more predetermined vibro-acoustic properties of the fluid and/or fluid path and communicate data on said measurements to the remote monitoring system.

4. The pipeline fault detection system of claim 3, wherein the remote monitoring system is arranged to perform signal correlation and filtering on data received from a sensor pair to screen for said characteristics.

5. The pipeline fault detection system of claim 4, wherein the remote monitoring system is arranged to estimate the velocity of acoustic waves propagating through the pipe in dependence on said received data from a sensor pair and on a measure of the distance along the pipeline that is between the sensors of the sensor pair.

6. The pipeline fault detection system of claim 1, wherein the vibro-acoustic sensor is mounted in a sensor head, the sensor head further comprising a geophone connected to a skin of the pipe and arranged to arranged to measure velocity of signals in the skin of the pipe and communicate data on said velocity of signals to the remote monitoring system, the sensor head further comprising a pressure sensor arranged to monitor fluid pressure and communicate data on said fluid pressure to the remote monitoring system.

7. The pipeline fault detection system of claim 6, further comprising a flow meter arranged to communicate data on fluid flow in the pipeline to the remote monitoring system, wherein the remote monitoring system is arranged to monitor for bursts in the pipeline in dependence on data from the flow meter and on data on the fluid pressure.

8. The pipeline fault detection system of claim 6, wherein the remote monitoring system is arranged to monitor for transient events in dependence on rate of change of pressure measured by said pressure sensor.

9. The pipeline fault detection system of claim 7, wherein the remote monitoring system is arranged to cross check a detected transient event against any data received from a flow meter to exclude the transient event being a pipe burst event.

10. The pipeline fault detection system of claim 1, further comprising a remote unit connected to the sensor via a data cable, the remote unit including a data communication system arranged to receive data on said measurements via said data cable from the sensor and arranged to communicate data on said measurements to the remote monitoring system.

11. The pipeline fault detection system of claim 1, wherein the or each vibro-acoustic sensor comprises a hydrophone.

12. The pipeline fault detection system of claim 1, wherein at least selected ones of the sensors perform measurements substantially continuously over at least a predetermined period and are arranged to collate data on said measurements and communicate said data to the remote monitoring system on a periodic basis.

13. The pipeline fault detection system of claim 11, wherein upon data of a predetermined characteristic being detected, the or each sensor being arranged to communicate data on the predetermined characteristic with the remote monitoring system outside of the periodic basis.

14. A sensor head including a body connectable to a fluid path passing through a pipe of a trunk mains pipeline, the sensor head including a hydrophone arranged to be in direct contact with fluid when the body is connected to the fluid path, the hydrophone being configured to measure, for a plurality of days and for a predetermined time period each day, the predetermined time period being less than 24 hours, one or more predetermined vibro-acoustic properties of the fluid and/or fluid path of the trunk mains pipeline when the trunk mains pipeline is online and under normal operating conditions so as to avoid interruption of a supply of water through the trunk mains pipeline, the sensor head being arranged to communicate data on each day's measurements to a remote monitoring system for building a representation of gradual changes in said pipeline's characteristics from the monitored data over said plurality of days, wherein building of the representation of gradual changes in said pipeline's characteristics from the monitored data over said plurality of days is a function of the monitored data from the predetermined time periods each being less than 24 hours.

15. The sensor head of claim 13, wherein the sensor head when connected to the fluid path is also connected to a skin of the pipe, the sensor head further comprising a geophone arranged to measure velocity of signals in the skin of the pipe, wherein the sensor head when connected to the fluid path is also connected to a skin of the pipe, the sensor head further comprising an accelerometer arranged to measure velocity of signals in the skin of the pipe and a pressure sensor.

16. The sensor head of claim 14, further comprising a heating system configured to heat the sensor head.

17. A method of detecting fault events in a trunk mains pipeline comprising:
measuring for a plurality of days and for a predetermined time period each day, the predetermined time period being less than 24 hours, using a vibro-acoustic sensor connected to a trunk mains pipeline having a fluid moving in a fluid path, one or more predetermined vibro-acoustic properties of the fluid and/or fluid path of the trunk mains pipeline when the trunk mains pipeline is online and under normal operating conditions so as to avoid interruption of a supply of water through the trunk mains pipeline;
communicating data on each day's measurements to a remote monitoring system;
monitoring said data over time;
building a representation of gradual changes in said pipeline's characteristics from the monitored data over said plurality of days, wherein the building of the representation of gradual changes in said pipeline's characteristics from the monitored data over said plurality of days is a function of the monitored data from the predetermined time periods each being less than 24 hours; and
screening the one or more of the representation and the monitored data for characteristics representing a fault type to identify occurrence of a fault event in the pipeline.

18. The method of claim 17, further comprising predicting the occurrence of a future fault event in dependence on one or more of the representation or the monitored data.

19. The pipeline fault detection system of claim 1, wherein the sensor is configured to record the data on the measurements during the predetermined period of time and subsequently upload the data to the remote monitoring system after the predetermined period of time.

20. The pipeline fault detection system of claim 1, wherein the remote monitoring system is configured to screen one or more of the representation and the monitored data for characteristics representing a fault type that are consistently present in the monitored data over said plurality of days.

* * * * *